United States Patent [19]

Foster et al.

[11] 4,117,250

[45] Sep. 26, 1978

[54] CONTINUOUS PROCESS FOR PRODUCING ALKYLENE GLYCOLS FROM ALKYLENE CARBONATES

[75] Inventors: Robert Dean Foster; Thomas Arthur Maliszewski, both of Charleston; Joseph Alton Sims, Jr., Elkview, all of W. Va.; Glenn Alfred Taylor, Ridgewood, N.J.

[73] Assignee: Union Carbide Corporation, New York, N.Y.

[21] Appl. No.: 863,352

[22] Filed: Dec. 22, 1977

[51] Int. Cl.² .............................................. C07C 29/12
[52] U.S. Cl. .................................................. 568/858

[58] Field of Search ........................ 260/635 E, 635 R

[56] References Cited

U.S. PATENT DOCUMENTS 3,629,343   12/1971   Levin et al. ..................... 260/635 E Primary Examiner—Joseph E. Evans
Attorney, Agent, or Firm—Donald M. Papuga

[57] ABSTRACT

A continuous process for hydrolyzing alkylene carbonates according to specific procedure whereby the akylene glycol obtained is essentially free of polymeric glycols and contains minimum amounts of dimeric glycols.

15 Claims, 1 Drawing Figure

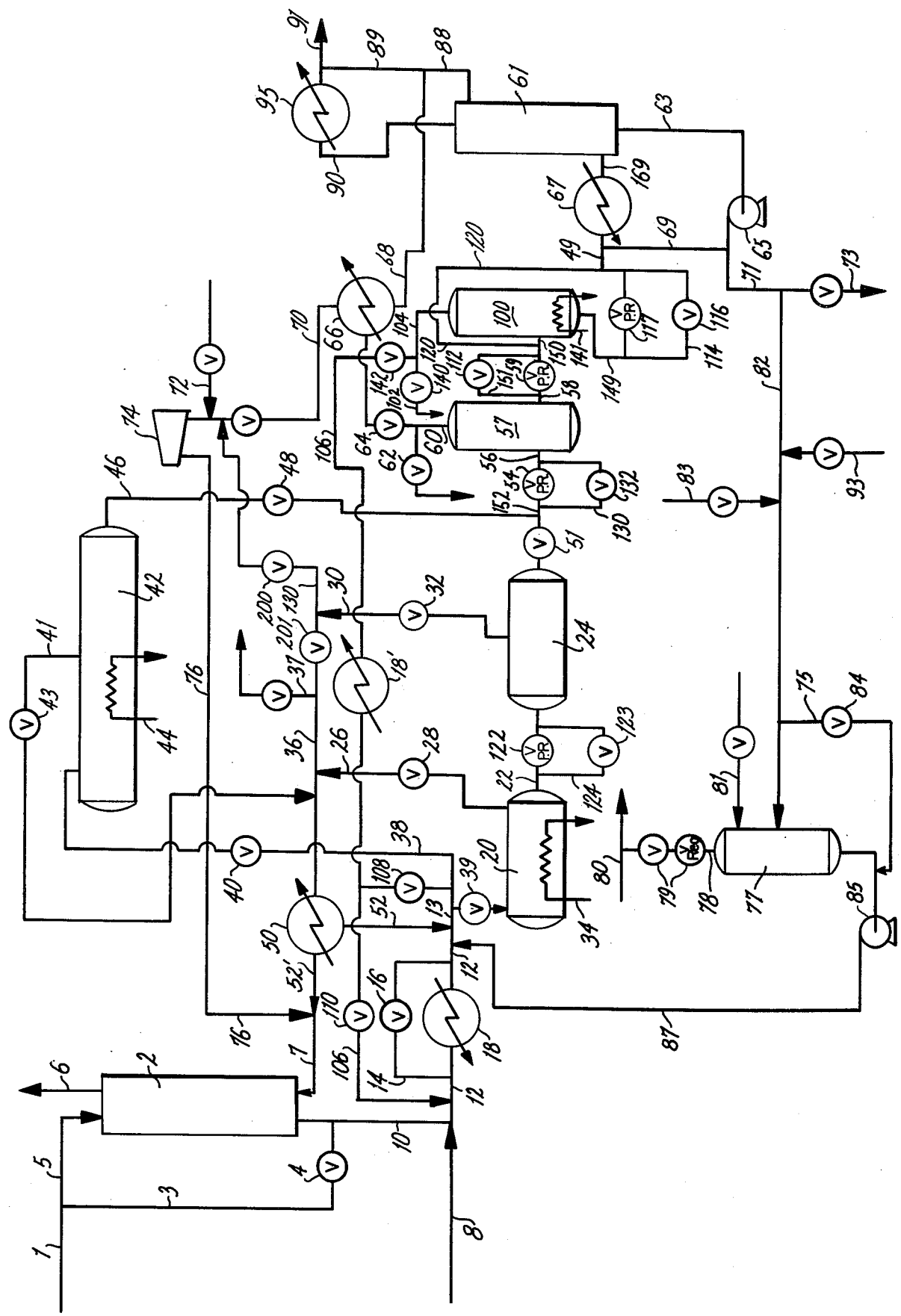

CONTINUOUS PROCESS FOR PRODUCING ALKYLENE GLYCOLS FROM ALKYLENE CARBONATES

This invention relates to a continuous process for the manufacture of 1,2-alkylene glycols, such as ethylene glycol and propylene glycol, by the hydrolysis of the corresponding alkylene carbonates, such as ethylene carbonate and propylene carbonate. More particularly, this invention involves the catalytic hydrolysis of such alkylene carbonates in the presence of carbon dioxide utilizing recycle of catalyst and some of the reaction product. Most desirably, this invention is directed to a continuous process for the production of a polyester grade of ethylene glycol by the hydrolysis of ethylene carbonate.

The prior art states that alkylene carbonates can by hydrolyzed to produce the corresponding alkylene glycol. For example, Peppel, *Industrial and Engineering Chemistry*, Volume 50, Number 5 (May, 1958), pages 767–770, describes, on page 769, that "Hydrolysis of ethylene carbonate is accelerated greatly by bases and to a much lesser extent by acids." In Table III, on page 769, the author indicates that sodium carbonate and sulfuric acid catalytically induce the hydrolysis of alkylene carbonates. In Table IV, at page 770, the author mentions that an azeotrope of ethylene glycol and ethylene carbonate occurs.

There is no known process described in the prior art for the continuous manufacture of ethylene or propylene glycols by the continuous hydrolysis of ethylene or propylene carbonates. Certain prior art exists which discloses the utilization of ethylene oxide as the starting material and effects hydrolysis of the ethylene oxide in the presence of carbon dioxide, Such prior art, viz., U.S. Pat. No. 3,629,343, patented Dec. 21, 1971, to Levin et. al., speculates that hydrolyzing ethylene oxide in the presence of water and carbon dioxide forms, in some instances, a transitory ethylene carbonate intermediate which is hydrolyzed to ethylene glycol. According to this patent, basic compounds such as carbonates, bicarbonates or hydroxides of alkali metals are utilized for the purpose of diminishing "the formation of dialkylene glycols and accelerate the reaction", see column 2, lines 26–30, of U.S. Pat. No. 3,629,343. In the practice of that process, such basic compounds are employed in combination with halo salts of tetralkylammonium compounds. The examples in this patent illustrate the basic compounds as including sodium bicarbonate, potassium bicarbonate, sodium carbonate, and sodium hydroxide.

The subject matter of this patent has been carefully reviewed by the Stanford Research Institute, in the private report entitled "Ethylene Glycols, Glycol Ethers and Ethanolamines," Process Economic Program, Report No. 70 (1970) and in the private report entitled "Ethylene Glycol", Process Economics Program, Report No. 70A Supplement (October 1975). In report No. 70, a careful consideration was given to British Pat. No. 338,026, published in 1970, which corresponds to U.S. Pat. No. 3,629,343. The author of the report notes the postulation of the reactions which take place in the process of the aforementioned British patent, which is, the reaction of ethylene oxide with carbon dioxide to form ethylene carbonate and the hydrolysis of the ethylene carbonate to form ethylene glycol. According to the patent, these reactions are effected simultaneously. However, in a continuous operation employing multiple reactors, the first reactor involves the utilization of a carbonation catalyst and carbon dioxide and the second reactor, in series with the first, employs hydrolysis using various bases. Report No. 70 attempts to characterize a continuous process from the meager data which is contained in the aforementioned British Patent. In characterizing a continuous process, the report points out that the water to oxide feed ratios were 1.04 to 1 and 1.06 to 1 in the two examples demonstrating a continuous process. In the second reactor, in which the base, water and carbon dioxide were provided, the temperature was 200° C. and the pressure in the whole system was 25 to 30 atmospheres, that is, 367.5 pounds per square inch to 441 pounds per square inch, respectively. According to the authors of the report, the British patent "is the only reference found dealing with glycol production by this method." The author of the report also notes that there are several references to the formation of alkylene carbonates by the reaction of alkylene oxides and carbon dioxide.

The report then attempts to design a process for carbonation and hydrolysis simultaneously, as described in the patent, utilizing the information reported in the patent. According to the author of the report, it is believed that much of the critical materials of construction will have to be expensive Monel ® clad construction. Though the authors of the report consider "the process design just described—as speculative" they did make a design which they consider to be based on "conservative assumptions." In characterizing the continuous process that they have discussed in the report, there is an assumption that 90% of the catalyst can be recycled which is regarded as economically important. In defining catalyst recycle, the following is stated:

"The system for catalyst recycle, based on crystallization from the cooled, heavy ends, with recycle of a thickened catalyst slurry, is quite uncertain, requiring data on solubility relationships and other factors, which are not available."

At page 71 of the report, a comparison is made of the product distribution obtained for two processes for making monoethylene glycol. The first process is pressurized hydrolysis involving the direct hydrolysis of ethylene oxide and the other process is the carbonation process which is embodied in their proposed scheme based upon the process of the aforementioned British Pat. No. 338,026 and its counterpart U.S. Pat. No. 3,629,343. In comparing the two processes, the pressurized hydrolysis process is indicated to produce about 88.1 weight percent monoethylene glycol, 9.4 weight percent diethylene glycol and 2.5 weight percent of triethylene glycol. The carbonation process, on the other hand, is contemplated to produce 98.1 weight percent of monoethylene glycol, 1.9 weight percent of diethylene glycol and no triethylene glycol.

In comparing the process of making monoethylene glycol from ethylene oxide by hydrolysis with that via the carbonation process, it is indicated that considerable savings in water removal can be achieved utilizing the carbonation process. FIG. 5.1 of the report schematically illustrates equipment and process design for making "ethylene glycols by carbonation process." This description provides a number of interesting points which indicate the impossibility of the characterized process in the report and the process of U.S. Pat. No. 3,629,343 to produce ethylene glycol which is of polyester grade, that is, ethylene glycol which can be used in making polyester fibers, i.e., polyethylene terephthalate.

According to the process design as set forth in said FIG. 5.1, ethylene oxide is combined with water, catalyst and carbon dioxide and fed to the bottom of a "carbonation reactor." It is introduced at a temperature of 200° F. (94° C.) and a pressure of 480 psig. Part of the product of reaction in the column is withdrawn from the top of the column and recycled back with the aforementioned feed, after going through a "carbonation reactor cooler." The overhead from the "carbonation reactor" is at 248° F. (120° C.) and is fed through a "hydrolysis reactor preheater" to raise the temperature to 448° F. (231° C.) and then fed to the bottom of the "hydrolysis reactor." The effluent from the top of the "hydrolysis reactor" is at 392° F. (200° C.) and 440 psig and is thereafter fed to a "separator." At no time in characterizing the reaction is there any indication that volatile materials formed in the carbonation step must be removed after or at the carbonation step. As pointed out in copending U.S. patent application Ser. No. 863,354 filed on Dec. 22, 1977, during the carbonation of ethylene oxide there are a number of volatiles produced, such as acetaldehyde, which has a capability of entering into polymer formation and forming ultra violet absorbers. If these volatiles are not removed at an appropriate time, the resulting ethylene glycol produced is incapable of passing the specifications for polyester grade.

Further consideration of FIG. 5.1 serves to demonstrate that the proposed continuous process depicted would be, for all practical purposes, incapable of producing any significant quantity of ethylene carbonate whereby the hydrolysis reaction would result from the hydrolysis of ethylene oxide or a halohydrin derivative and not of ethylene carbonate. On the basis of a careful analysis of that process, it is submitted that most of the hydrolysis which occurs in the "hydrolysis reactor" would not be of the ethylene carbonate. In this regard, the following consideration should be taken into account:

The reaction at the inlet of the carbonation reactor is 200° F., that is 93° C. Japanese Publication No. 38-23-175/63 published Oct. 31, 1963, shows in Examples 1 and 2 thereof, the use of sodium bromide as a catalyst for the carbonation of ethylene oxide operated at a highest temperature of 165° C. and approximately 149 atmospheres pressure. In carrying out the process, the Japanese applicants put the ethylene oxide, carbon dioxide and sodium bromide catalyst into an autoclave and heat to elevate the pressure gradually to achieve maximum pressure. In the first example, they found that when the temperature exceeded 160° C., the pressure began to drop and heating was continued to 180° C. as the highest temperature, then heating was discontinued. In Example No. 2, following that same procedure, using sodium bromide catalyst, the authors employed a maximum of 165° C. In USSR Pat. No. 170,529, issued to Levin and Shapiro, the examples describe the use of alkali metal bromides and chlorides as catalysts for the carbonation of ethylene oxide. It is characterized therein that when using sodium chloride to carbonate a mixture of ethylene oxide and carbon dioxide, the reaction takes place in a temperature range of 210°–215° C., utilizing an initial pressure of 120 atmospheres. In another example utilizing ethylene carbonate in combination with ethylene oxide in the presence of carbon dioxide with potassium bromide catalyst, the temperature employed was 170°–180° C. Example 3 of that patent reacted ethylene oxide with carbon dioxide (absent ethylene carbonate) utilizing potassium bromide as a catalyst and they state that "the reaction takes place at a higher temperature (210°–230° C.) and at a lower rate (taking 28 minutes)."

Thus, the authors of the Stanford Research report No. 70 employ in FIG. 5.1 a starting temperature of 93° C., which is considerably lower than that which has been characterized by other authorities in the field, and reach the highest temperature in the carbonation reactor of 120° C. This would indicate that very little ethylene carbonate formation has occurred in the "carbonation reactor" and that much of the ethylene glycol production is being effected by the hydrolysis of ethylene oxide or a halohydrin derivative, by the carbonic acid salt as catalyst. Thus, U.S. Pat. No. 3,629,343, with the same inventorship as the aforemention USSR Pat. No. 170,529, described above, seems to contradict the USSR patent unless one takes the position that the lower temperatures which are depicted in the equation in column 2 of the U.S. patent are contemplated to occur utilizing catalysts which are different from the catalysts selected by the Stanford Research report as set forth in the said FIG. 5.1. However, even that proposition does not seem to be valid when one considers the work of Peppel, supra, who states at page 767 that "The reaction of ethylene oxide with carbon dioxide is initiated by the quaternary ammonium halides at about 150° to 175° C." As a consequence we have a direct confrontation between this statement in Peppel, supra, and that which is set forth in U.S. Pat. No. 3,629,343. It is submitted that the Stanford Research report does not resolve this conflict.

The process of this invention constitutes a wholly new approach for the continuous manufacture of alkylene glycol by the hydrolysis of alkylene carbonate. This approach avoids the production of polymeric glycols which attend the hydrolysis of ethylene oxide, as noted previously, and produces relatively insignificant amounts of diethylene glycol, as compared with the conventional process for manufacturing ethylene glycol by the hydrolysis of ethylene oxide. In addition, the process of this invention produces less than one half the amount of diethylene glycol which is reported in U.S. Pat. No. 3,629,343. Indeed, the amount of diethylene glycol which can be produced in accordance with the process of this invention can be reduced to less than one half of that figure. The process of this invention does not suffer from any problem in catalyst recycle and can be carried out in conventional metal equipment, such as stainless steel. It can also achieve exceptional efficiencies and conversion rates. Most importantly, the process of this invention can be utilized to produce ethylene glycol which when catalyst and water are removed, can meet the stringent requirements of Polyester Fiber Grade (see companion application Ser. No. 863,854, filed on Dec. 22, 1977, for a definition thereof). Thus, as a result of the process of this invention, one can produce quite easily, a Polyester Grade ethylene glycol. A further advantage, one which is recognized in the Stanford Research Institute report, No. 70, is that all of this can be achieved with the use of substantially less water than must be employed in conventional processes for producing ethylene glycol by the hydrolysis of ethylene oxide.

Other advantages of the process of this invention are that it does not require the utilization of any catalyst slurry in recycling catalyst; the reaction is exceptionally rapid and efficient in the direction of monoethylene glycol or monopropylene glycol; the hydrolysis can be utilized using waste water obtained from industrial reactions, such as, the scrubber waters in ethylene oxide production, thereby providing an ecological advantage through the operation of the process. In addition, the present process can be coordinated directly to an ethylene carbonate reaction system, such as described in copending application Ser. No. 863,354, whereby spent carbon dioxide can be very efficiently recycled to an ethylene carbonate reactor without any further treatment or alternatively, cleaned and dried before said recycle.

The continuous process of this invention for the manufacture of alkylene glycol of the formula HOCHRCH$_2$OH, wherein R is hydrogen or methyl, by the base hydrolysis of an alkylene carbonate of the formula

OCHRCH$_2$OC=O comprises the following steps:

(A) providing the alkylene carbonate in admixture of water, carbon dioxide, alkylene glycol and potassium carbonate catalyst, to form a homogeneous liquid phase mixture;

(B) providing said mixture in a reaction zone wherein the temperature of said mixture is at least 100° C.;

(C) evolving carbon dioxide from said homogeneous liquid base mixture;

(D) separating the potassium carbonate catalyst in admixture with alkylene glycol from alkylene glycol product;

(E) recycling said catalyst-glycol mixture to step (A); and (F) periodically feeding potassium carbonate catalyst make-up to said catalyst-glycol mixture before it is fed to step (A), cited above.

The catalyst employed in practicing the process of this invention may be any potassium compound which when incorporated into protic medium under carbon dioxide pressure produces potassium carbonate, either as the ionic form or potassium bicarbonate form.

In the preferred practice of this invention, potassium carbonate under CO$_2$ should be employed as the catalyst. If, however, one attempts to initiate the reaction, i.e. hydrolysis reaction, by the use of potassium hydroxide, a substantial amount of hydroxide ion is present during the initial part of the hydrolysis reaction which can attack the alkylene carbonate causing significant amounts of it to be decomposed in such a manner as when those materials undergo hydrolysis in the presence of hydroxide ion in the system, much greater amounts of diethylene glycol and polymeric ether glycols will be produced and as such are considered undesirable in practicing the process of this invention. This unique effect of potassium carbonate and CO$_2$ upon the hydrolysis of ethylene carbonate in order to produce essentially monoethylene glycol is not in the literature. Although alkali metal carbonates, as a class have been suggested for the purposes of hydrolysis, there is an unique synergistic result obtained from the use of potassium carbonate and CO$_2$ because it will produce monoethylene glycol more rapidly than will any of the other alkali metal carbonates and bicarbonates. In addition, potassium carbonate is considerably more soluble in ethylene glycol so that it can be recycled as a solution rather than as a slurry to effect continuous hydrolysis of incoming alkylene carbonate. This advantage is not characterized in the prior art, see the Stanford Research report No. 70, which contemplates recycling slurries of catalyst.

The amount of catalyst which is provided with the initial feed of the alkylene carbonate may range between about 0.03 to about 10 weight percent, based on the weight of alkylene carbonate fed to the reaction. Preferably, the amount of the catalyst is about 0.10 to about 5.0 weight percent, and most preferably, the greatest catalytic effect, for the amount of catalyst employed, is achieved when the catalyst amount ranges between 0.25 and about 1.5 weight percent, based on the weight of alkylene carbonate. In characterizing the catalyst concentration, it has been characterized in terms of potassium carbonate.

The temperature which is necessary to initiate hydrolysis of the alkylene carbonate can be as low as 85° C. and one might comtemplate that the maximum temperature is about 400° C. However, it is preferred that a minimum temperature of 100° C. be employed and that the maximum temperature be kept below 300° C. In the most preferred operation of the reaction, it is desired that the temperature be between about 120° C. and about 200° C.

The pressure at which the reaction is carried out should be greater than about 80 psig. There appears to be no apparent maximum from the standpoint of achieving the ultimate efficiency and conversion rates as set forth herein. However, from a practical commercial standpoint, the maximum pressure should not be greater than about 2,000 psig. In a commercial operation where saving in cost of operation and equipment are paramount considerations, pressures below about 1,000 psig and preferably below about 750 psig are extremely attractive. These practices and considerations are not to be construed as limits on the commercial practice of this invention, but a processor who is planning to build a plant, purchase new equipment, etc. would obviously prefer, from cost standpoint, to use the least costly equipment and therefore would desire to employ lower pressure reaction conditions. Such is possible with this invention. However, if the manufacturer possesses high pressure equipment which he wishes to convert, and also possesses the ability to attain such high pressures economically, then of course this process can be employed under such conditions. Higher pressures typically will reduce the reaction rate but at the same time will also reduce the heat loads required in order to maintain the temperature of the reaction.

The initial mole ratio of water to alkylene carbonate which is employed in the hydrolysis reaction, that is, the amount of water which is combined with the alkylene carbonate in the reaction zone in order to effect hydrolysis, should be at least one mole of water per mole of alkylene carbonate. However, from a practical standpoint, in order to achieve the kind of performance characterized for the process of this invention, one should employ at least about 1.2 moles of water and at most about 10 moles of water for each mole of alkylene carbonate. The most preferred ratio is about 1.5 to 2.5:1. For example, when that mole ratio is below about 1.2, in the hydrolysis of ethylene carbonate, it becomes very difficult to produce polyester grade ethylene glycol. In addition, mole ratios below 1.2 make it difficult to minimize the production of diethylene glycol or dipropylene glycol.

In order to more definitively describe many of the embodiments of this invention, reference is made to the drawing which schematically depicts a process flow diagram of a desirable embodiment of this invention. In discussing this flow diagram, the various permutations and combinations which are within the purview of this invention will also be discussed.

With reference to the drawing, line 1 is connected to a source of supply of alkylene carbonate. Hereinafter reference will be specifically made to ethylene carbonate as the alkylene carbonate for the purposes of specificity and a clearer definition of the invention. The source of ethylene carbonate is optional. The source may be a laboratory operation or commercial production. It may be obtained from essentially any kind of commercial operation such as is characterized by the prior art. However, if it is ethylene carbonate, such as produced by the prior art then it is desirable that it be carefully distilled in order to remove all impurities so as not to jeopardize the ability of the instant process to produce polyester grade ethylene glycol. Most preferably, the ethylene carbonate is one which is produced according to the process which is described in copending applications Ser. No. 863,354, filed Dec. 22, 1977, and as refined according to the process in copending application, Ser. No. 863,353, filed Dec. 22, 1977. If made in accordance with the procedures as set forth in these referred applications, the ethylene carbonate can be readily employed in the process of this invention to produce polyester grade ethylene glycol without any difficulty.

The ethylene carbonate so obtained, is transmitted via line 1 to line 3, then through valve 4 to line 10. In a preferred embodiment of this invention, the alkylene carbonate can be employed for the purpose of drying wet carbon dioxide which is generated in the hydrolysis process. In such an embodiment, the ethylene carbonate from line 1 is passed to line 5, valve 4 is closed, and the ethylene carbonate is fed to the top of a $CO_2$ drying column (as described in copending patent application Ser. No. 863,355, filed Dec. 22, 1977, desirably supplied with materials to effect diffusion and dispersion of countercurrently supplied carbon dioxide, which is supplied through line 7 into $CO_2$ drying column 2 and upwardly therethrough to be removed via line 6. This dry carbon dioxide can thereafter be recycled to any industrial unit utilizing dry $CO_2$, such as described in the aforementioned copending U.S. patent application Ser. No. 863,354. As an alternative, if the instant process for manufacturing ethylene glycol by the hydrolysis of ethylene carbonate is not tied to a unit utilizing dry $CO_2$, then the wet carbon dioxide formed in the hydrolysis reaction need not be passed through the $CO_2$ drying column. One of the advantages of the $CO_2$ drying column is that it is an energy saving method for removing water, with a material employed in the reaction. At the same time, this saves in the employment of make-up water in the reaction because the ethylene carbonate will carry the water that is removed from the $CO_2$ back into the reactor where hydrolysis occurs. In addition, the ethylene carbonate reclaims at least a part of the heat which is contained in the wet carbon dioxide passed into $CO_2$ drying column 2 through line 7. The ethylene carbonate passed through either line 3 or through the $CO_2$ drying column 2, is then sent to line 10. Water is supplied to line 10 through line 8 to provide the predominant amount of water which is necessary for effecting hydrolysis. The combination of lines 8 and 10 form line 12 which is connected to a preheater 18 for the purpose of supplying the necessary heat for effecting the reaction, or at least a portion of that heat for effecting the reaction. Recycle water from tank 100 can be supplied to line 12 via lines 104 and 106. However, if the heat is to be achieved by other means, then the preheater can be bypassed by passing the contents of line 12 to line 14 containing valve 16. Valve 16 controls the flow and renders line 14 an optional line for effecting an additional variation in the practice of this process. Thereafter, the contents resupplied or originally supplied to line 12 are combined with recycled catalyst from line 87, and optionally with water condensed from wet $CO_2$ passed from the carbon dioxide cooler 50 to line 52, and these are supplied to line 13. The contents of line 13 are very quickly passed to the reactor 20 since, if preheated, the reaction mixture will very quickly undergo reaction to effect production of ethylene glycol.

As described in the drawing, there are a number of reactor variations which may be employed in the practice of this invention. In the drawing, the basic reactor described is a plug-flow reactor. This does not mean that the process of this invention must be carried out in a plug-flow reactor. At least a part of the reaction may be effected in another type of reactor, such as a backmix reactor, or in a third reactor. However, it has been found that to obtain the ultimate efficiencies and conversions, as hereinafter described, the completion of the reaction is desirably achieved in a plug-flow reactor.

As shown in the drawing, two reactors 20 and 24 are employed in series. On the other hand, valve 39 can be shut and the contents of line 13 can be fed to line 38, depicted as fitted with valve 40 to shut off line 38 if not used, so that the reactants can be fed to a single plug-flow reactor 42 fitted with heater 44. Heater 44 is an optional heater or it may be used solely for the purposes of bringing the reactants to reaction temperature. One may use heater 44 with preheater 18 for the purposes of achieving reaction temperatures. However, if one employs the dual reactors 20 and 24 in series, or even more reactors in series, which is also feasible in accordance with the practice of this invention, then the contents of line 13 are fed into one end of reactor 20, which is optionally heated by heater 34.

Heaters 34 and 44 may be steam or electrical heaters.

As the reaction progresses, one has the option of removing the evolved carbon dioxide from the reactors. This can be accomplished, in the case of reactor 42, through line 41 containing valve 43, thereby making the removal an optional feature. With respect to reactor 20, wet carbon dioxide can be removed through line 26, which contains valve 28. The product of the reaction in reactor 20 is thereafter removed via line 22, with or without the evolved carbon dioxide, into reactor 24. The pressure in reactor 24 may be less than that of reactor 20 by passing it through pressure reducing valve 122 or alternatively, the pressure of reactor 24 may be the same as 20 by passing through valve 123 via line 124. Reactor 24 is desirably an adiabatic reactor. Reactor 24 is fitted with line 30, which contains valve 32, for removing carbon dioxide, which removal is optional. In the usual case, such evolved carbon dioxide is removed directly from the reactors 42, 20 and 24 through lines 41, 26 and line 30, respectively, to either be vented through line 37 containing a valve, or passed via line 36 into an optional piece of equipment, which is carbon dioxide cooler 50. If reactor 24 is operated at a lower pressure than reactor 20, per the option above, than the $CO_2$ vent from this reactor may be passed via line 130 through valve 200 to the suction of compressor 74, valve 201 would then be closed. Condensed liquid from the $CO_2$ cooler 50 can pass from line 52 into line 13. The wet carbon dioxide removed from carbon dioxide cooler 50 is transmitted by line 52' to which may be added additional carbon dioxide supplied through line 76 which passes through compressor 74 from line 72, to line 7 and into $CO_2$ drying column 2, as described previously.

The product of the reaction is removed from reactor 24, or any other plug-flow reactor utilized in series with reactor 24, through valve 51 or removed from reactor 42 via line 46 through valve 48, and passed through line 152 to a pressure reducing valve 54. Optionally the pressure reducing valve 54 may be bypassed through line 130 containing valve 132, then passed into line 56. The reaction product is then passed through line 56 and introduced into flash tank 57, operated at reaction pressure or less, for the purpose of removing gases and some water which is present in the mixture. If water which is fed to the reaction through line 8 is, for example, scrubber water, then it is possible that the flash tank will also remove some of the volatiles carried into the system with the scrubber water. These volatiles can be vented through line 60 and valve 62, or the valve 62 can be closed and the valve 64 is open to pass the gasses to cooler 66 to remove heat from the $CO_2$ for subsequent compression. The noncondensed vapor removed from cooler 66 is fed by way of line 70 to a valve, then to compressor 74. Additional carbon dioxide may be added to compressor 74 by way of line 72 containing a valve. The compressed gas is thereafter passed to line 76 which combines it with stream 52' removed from cooler 50.

Liquid contents from flash tank 57 flow through line 58 and pressure reducing valve 59 and can then be passed directly into evaporator 61 through line 120, to line 49, through cooler 67 and then through line 169, or alternatively the outlet of pressure reducing valve 59 can go into tank 100 equipped with a heater 141 through line 150. Heater 141 may be either steam or electric. Pressure reducing valve 59 can be bypassed by passing the contents from line 58 to line 151 containing valve 112, to line 150 or line 120. A portion of the water evaporated from the reactor stream in tank 100 can be recycled to reactor 20 or 42 via line 104 into line 106 through cooler 18' into line 12, which is then passed through preheater 18. Alternatively, the recycle water can be added after the preheater 18, by closing valve 110 and opening valve 108 via line 104, line 106 and cooler 18'. An energy conservation option would combine heat exchanger 18 and 18' to recover the heat from stream 106 by preheating stream 12. As an option, the water stream removed via line 104 from flash tank 100 can be sewered via line 102 by closing valve 142 and opening valve 140. The removal of a portion of the water in flash tank 100 for recycle or sewerage adds the advantage of reducing the volume of liquid passed through a refining unit, while maintaining the water to ethylene carbonate mole ratios at desirable levels. Thus, if this option is used, a smaller refining unit(s) can be utilized then otherwise demanded.

The only undesirable affect of recycling reaction water in this manner is caused by impurities introduced initially in the reactants building up, and causing a purge to be taken which would result in loss in efficiency due to the loss of glycol contained in this purge stream. Line 102 can serve as the purge stream. The contents of flash tank 100 is added to evaporator 61 via line 149 through heater 67 and lines 49 and 169. Line 149 can be operated either through the pressure-reducing valve 117 or bypassing this pressure-reducing valve via line 114 containing valve 116.

Evaporator 61 is typically operated at reduced pressure and it is heated by circulation in the bottom. The temperature of evaporator 61 is maintained by removing the base product therefrom via line 63, passing it through pump 65 into line 69 and combining it with line 49, passing it through heater 67 and into evaporator 61 by line 169.

Predominant amounts of the ethylene glycol produced are removed from the evaporator 61. Part of the ethylene glycol and diethylene glycol produced is collected in the base of the evaporator along with the catalyst. This mixture is removed from the bottom of evaporator 61. It is important that the concentration of the catalyst at the bottom of the evaporator be held to a minimum to avoid the possibility of forming potassium glycolate. The ethylene glycol products removed from the top of evaporator 61 are passed by way of line 90 through cooler 95. Most of the stream is removed as the crude ethylene glycol product through line 91. Some of the ethylene glycol products can be passed through line 89 and combined with liquid condensate fed through line 68 to form a line 88 to provide reflux to evaporator 61. The preferred embodiment for evaporator 61 is a column with trays; other separating devices may be employed to remove the ethylene glycol from the reaction effluent.

The catalyst recovered from the bottom of evaporator 61 is a concentrate of potassium carbonate in glycol. It is removed via lines 63 and 71 and optionally purged through line 73. This purge typically is not more than about 10 weight percent of stream 71 and is dependent upon the amount of impurities which are found to be contained in the reactors, determined mainly by analysis of the incoming feed and represents a corrective measure for insuring that the product quality is maintained. It is important to recognize that impurities found in the system come mainly from the reactants and are not formed by the process itself.

Alternatively, product removed from evaporator 61 by line 63, passed through pump 65 into line 71 then into line 82 for return to the reactor.

Catalyst solution if not treated in a catalyst solution surge tank, may be treated with additional carbon dioxide introduced through a valve in line 93 and make-up catalyst in such a case could be supplied through line 83. However, it is most desirable to supply the recycle catalyst to surge tank 77 which is supplied with make-up catalyst through line 81 and a carbon dioxide blanket fed through lines 80 and 78 which in turn contain pressure regulator valves 79. If surge tank 77 is to be bypassed, then the recycled catalyst solution from line 82 will pass to line 75 containing valve 84 into the line containing pump 85. However, when the surge tank 77 is employed, the catalyst solution from line 63 is supplied to tank 77. Catalyst is continuously removed from surge tank 77 and pumped through line 87 into line 12 to be combined with line 13 to produce a recycle mode, which is characteristic of this process.

There is no catalyst deactivation in the process of this invention. Catalyst make up is needed only when a purge is employed which removes the catalyst in ethylene glycol residue from evaporator 61. However, if no purge is taken, as indicated by existing line 73, then of course, make-up of catalyst in the surge tank is not necessary.

Typically in chemical processing there will be losses of catalyst in carrying out the process and in such a case, it will be desirable to provide some system for catalyst make-up.

The process of this invention in respect to the manufacture of ethylene glycol produces less than 1 weight percent of diethylene glycol, no triethylene glycol, and better than 99% of monoethylene glycol based on the total weight of products produced.

It is important to recognize that in carrying out the process of this invention, that whatever impurities produced which would render the resulting monoethylene glycol unsuitable to pass the polyester grade specifications, will be those impurities which were inherently present in the starting materials and not produced by the process itself. Thus, the use of extremely pure ethylene carbonate and pure water may be used in carrying out the process of this invention and this will insure that the ethylene glycol produced is polyester grade. However, with the use of "scrubber water," an impure purge water stream typically produced by an ethylene oxide unit, polyester grade ethylene glycol may be produced with proper product refining.

The following example is a characterization of the continuous process of this invention based upon the drawing.

For the purposes of the following description, "residues" refers to traces of polyethylene oxide and tetra- and higher ethylene glycols while "aldehydes" refers to volatile aldehydes (acetaldehyde, formaldehyde, crotonaldehyde, etc.) which are present as trace impurities in the feed stream.

Reactor 20 (a jacketed plug-flow reactor) is maintained at 170° C. and 550 psig. Ethylene carbonate is added through line 1 at the rate of 100.15 pounds per hour at 120° C. and 557 psia. The ethylene carbonate stream is composed of 99.93 weight percent ethylene carbonate and 0.07 wt. percent residues. This ethylene carbonate is fed to $CO_2$ drying column 2 (described in U.S. patent application Ser. No. 863,355, which is incorporated herein by reference), and exits as stream 10 at 107.30 pounds per hour at 105° C. and 560 psia. Line 10 contains 0.15 wt. percent water, 0.06 wt. percent residues, 6.51 wt. percent $CO_2$, 0.08 wt. percent aldehydes, and 93.20 wt. percent ethylene carbonate.

Water is added through line 8 at the rate of 35.68 pounds per hour at 85° C. and 100 psia. The water stream is composed of 98.75 weight percent water, 1.09 weight percent monoethylene glycol, 0.14 weight percent diethylene glycol, and 0.10 weight percent triethylene glycol, and traces of aldehydes.

The streams from lines 8 and 10 form the stream in line 12 supplied at 142.98 pounds per hour at 128° C. and 565 psia to preheater 18 operated at 170° C. The stream in line 12 contains 24.75 wt. percent water, 0.27 wt. percent monoethylene glycol, 0.03 wt. percent diethylene glycol, 0.4 wt. percent residues, 4.88 wt. percent $CO_2$, 69.92 wt. percent ethylene carbonate, and 0.06 wt. percent aldehydes. The stream of line 12 is heated to 170° C. in the preheater 18 (a heat exchanger).

After leaving the preheater, the stream in line 12 is combined with the stream from line 87, coming from catalyst surge tank 77, supplied at 15.65 pounds per hour at 120° C. and 560 psia (this stream contains 0.64 wt. percent water, 50.27 weight percent monoethylene glycol, 3.77 wt. percent diethylene glycol, 7.41 wt. percent triethylene glycol, 30.29 wt. percent residues and 7.67 percent potassium carbonate); the stream from line 52 coming from $CO_2$ cooler 50 (a heat exchanger) supplied at 3.51 pounds per hour at 60° C. and 560 psia (this stream contains 72.85 wt. percent water, 22.17 wt. percent monoethylene glycol, 0.08 wt. percent diethylene glycol, 0.03 wt. percent triethylene glycol, 2.15 wt. percent $CO_2$ 2.56 wt. percent ethylene carbonate, 0.15 wt. percent aldehydes) to form the stream in line 13.

The stream in line 13 is supplied to reactor 20, at 162.14 pounds per hour at 169° C. and 560 psia. This stream contains 23.47 wt. percent water, 5.57 wt. percent monoethylene glycol, 0.39 wt. percent diethylene glycol, 0.72 wt. percent triethylene glycol, 2.97 wt. percent residues, 4.35 wt. percent $CO_2$, 0.74 wt. percent potassium carbonate, 61.73 wt. percent ethylene carbonate, 0.06 wt. percent aldehydes.

The product of the reaction in reactor 20 is removed via line 22 and fed into reactor 24 (a jacketed plug-flow reactor). The stream in line 22 is fed into reactor 24 at 108.24 pounds per hour at 170° C. and 560 psia. This stream contains 15.90 wt. percent water, 65.92 wt. percent monoethylene glycol, 0.89 wt. percent diethylene glycol, 1.11 wt. percent triethylene glycol, 4.44 wt. percent residues, 1.37 wt. percent $CO_2$, 1.11 wt. percent potassium carbonate, 9.24 wt. percent ethylene carbonate, and 0.02 wt. percent aldehydes.

Wet $CO_2$ is directly removed from reactor 20 through line 26 and from reactor 24 via line 30. The $CO_2$ in line 26 is removed at 53.90 pounds per hour at 170° C. and 560 psia while the $CO_2$ in line 30 is removed at 5.52 pounds per hour at 170° C. and 558 psia. The $CO_2$ stream in line 26 contains 4.62 wt. percent water, 1.29 wt. percent monoethylene glycol, 93.79 wt. percent $CO_2$, 0.13 wt. percent aldehydes, and 0.17 wt. percent ethylene carbonate. The $CO_2$ stream in line 30 contains 4.0 wt. percent water, 1.52 wt. percent monoethylene glycol, 94.35 wt. percent $CO_2$ 0.11 wt. percent aldehydes. The $CO_2$ streams from lines 26 and 30 are supplied to the $CO_2$ cooler 50 via line 36. The stream in line 36 is supplied to the $CO_2$ cooler at 59.42 pounds per hour at 160° C. and 558 psia. The stream in line 36 contains 4.56 wt. percent water, 1.31 wt. percent monoethylene glycol, 93.84 wt. percent $CO_2$, 0.14 wt. percent aldehydes and 0.15 wt. percent ethylene carbonate. Cooler 50 is maintained at 120° C. The vapor from cooler 50 is removed via line 52' at a flow rate of 55.91 pounds per hour at 120° C. and 557 psia with a composition of 0.27 wt. percent water, 99.59 wt. percent $CO_2$ and 0.14 wt. percent aldehydes. This flow is mixed with stream 76 and passed to $CO_2$ drying column 2 via line 7. Stream 76 has a flow rate of 2.67 pounds per hour at 40° C. and 557 psia with a composition of 0.17 wt. percent water, 99.54 wt. percent $CO_2$ and 0.32 wt. percent inerts. Stream 7 is supplied to the $CO_2$ drying column at 58.59 pounds per hour at 124° C. and 557 psia. Line 7 contains 0.25 wt. percent water, 99.59 wt. percent $CO_2$ and 0.14 wt. percent aldehydes. Dryed $CO_2$ is removed from $CO_2$ drying column 2 via line 6. The dryed $CO_2$ is removed at 51.44 pounds per hour at 124° C. and 557 psia. The composition of line 6 is 99.84 wt. percent $CO_2$ and 0.16 wt. percent ethylene carbonate.

The product of the reaction in reactor 24 is removed via line 52 and passed into pressure reducing valve 54. The stream in line 152 is supplied into pressure reducing valve 54 at 102.72 pounds per hour at 160° C. and 558 psia. The composition of the stream in line 56 is 14.56 wt. percent water, 76.20 wt. percent monoethylene glycol, 0.97 wt. percent diethylene glycol, 1.17 wt. percent triethylene glycol, 4.68 wt. percent residues, 1.24 wt. percent CO$_2$, 0.01 wt. percent aldehydes and 1.17 wt. percent potassium carbonate. The pressure of the stream is reduced by pressure reducing valve 54 to 20 psia and then passed into flash tank 57 operated at 20 psia. Line 58 removes liquid product from flash tank 57 and then passes it through pressure reducing valve 59 via line 120 to line 49 through preheater 67 (falling film heater) and into evaporator 61 (a trayed evaporator) via line 169. The stream in line 58 is passed to pressure reducing valve 59 at 96.29 pounds per hour at 140° C. and 20 psia. The composition of the stream in line 58 is 11.32 wt. percent water, 80.15 wt. percent monoethylene glycol, 1.03 wt. percent diethylene glycol, 1.25 wt. percent triethylene glycol, 4.99 wt. percent residues and 1.25 wt. percent potassium carbonate.

The gases from the flash tank 57 are removed via line 60 into cooler 66, removed therefrom by line 70 through a valve and into compressor 74. The gases in line 60 are removed at 6.42 pounds per hour at 140° C. and 20 psia. The stream in line 60 contains 62.94 wt. percent water, 17.05 wt. percent monoethylene glycol, 0.04 wt. percent diethylene glycol, 0.01 wt. percent triethylene glycol, 19.78 wt. percent CO$_2$, 0.17 wt. percent aldehydes. Cooler 66 is at 40° C. Condensate is removed via line 68 and passed into line 88. Product is removed via line 68 at 5.11 pounds per hour at 40° C. and 18 psia. The composition of the stream in line 68 is 78.38 wt. percent water, 21.40 wt. percent monoethylene glycol, 0.05 wt. percent diethylene glycol, 0.01 wt. percent triethylene glycol, 0.10 wt. percent CO$_2$ and 0.04 wt. percent aldehydes. The material in line 70 is fed into compressor 74 at 1.31 pounds per hour at 40° C. and 18 psia.

Additional CO$_2$ at 1.42 pounds per hour, 40° C. and 19.5 psia is passed into compressor 74 via line 72. The stream in line 72 contains 2.35 wt. percent water and 97.65 wt. percent CO$_2$. The product from the compressor is removed via line 76 which combines it with the carbon dioxide in stream 52' removed from cooler 50, as mentioned previously.

Evaporator 61 is operated with base conditions of 150° C. and 170 millimeters of mercury pressure. Catalyst in a portion of the ethylene glycol product is removed from the bottom of the evaporator via line 63 at 857.12 pounds per hour at 150° C. and 170 millimeters of mercury pressure. The composition of the product in line 63 is 0.39 wt. percent water, 50.42 wt. percent monoethylene glycol, 3.78 wt. percent diethylene glycol, 7.44 weight percent triethylene glycol, 30.40 wt. percent residues, and 7.57 wt. percent potassium carbonate. Product in line 63 is passed through pump 65 and then split between line 69 and line 71 and a purge is taken through line 73. The remainder of the stream in line 71 is passed into line 82 to surge tank 77. Lines 69, 71, 73 and 82 have compositions identical to that of stream 63, listed above. The product in line 71 is supplied at 15.85 pounds per hour at 148° C. and 50 psia. The purge taken via line 73 is at 0.26 pounds per hour at 148° C. and 50 psia. Line 82 has a flow of 15.59 pounds per hour at 148° C. and 50 psia.

Make up catalyst can be supplied to surge tank 77 by line 81. This catalyst is supplied at 0.06 pounds per hour at 40° C. and 565 psia. The composition of this stream is 67.00 wt. percent water and 33.00 wt. percent potassium carbonate.

The part of the product from line 63 going into line 69 is at 841.28 pounds per hour at 148° C. and 50 psia. This flow is combined with line 49 and passed through preheater 67 and into evaporator 61 by line 169. The stream in line 169 is supplied at 937.57 pounds per hour at 150° C. and 185 mm mercury pressure. The stream in line 169 contains 1.51 wt. percent water, 53.47 wt. percent monoethylene glycol, 3.50 wt. percent diethylene glycol, 6.80 wt. percent triethylene glycol, 27.79 wt. percent residues and 6.92 wt. percent potassium carbonate.

The ethylene glycol products are removed from the top of evaporator and passed via line 90 through cooler 95. The products are passed into line 90 at 89.00 pounds per hour at 138° C. and 155 millimeters of mercury. The composition of the stream in line 90 is 17.36 wt. percent water, 82.15 wt. percent monoethylene glycol, 0.46 wt. percent diethylene glycol, 0.02 wt. percent triethylene glycol and 0.01 wt. percent CO$_2$. Cooler 95 is at 122° C. The stream exiting the cooler is split into stream 91, at 85.55 pounds per hour, at 75° C. and 150 mm mercury pressure, and stream 89 at 3.45 pounds per hour at 75° C. and 150 mm mercury pressure. The composition of these streams is identical (17.36 wt. percent water, 82.15 wt. percent monoethylene glycol, 0.46 wt. percent diethylene glycol, 0.02 wt. percent triethylene glycol and 0.01 wt. percent CO$_2$).

The portion of the product leaving cooler 95 as line 89 is then combined with the product in line 68, coming from cooler 66, and passed into evaporator 61 via line 88. The stream in line 88 is passed into evaporator 61 at 8.56 pounds per hour at 40° C. and 155 mm mercury pressure. The contents of the stream in line 88 are 53.66 wt. percent water, 45.79 wt. percent monoethylene glycol, 0.2 diethylene glycol and 0.12 wt. percent CO$_2$.

What is claimed is:

1. A continuous process for making glycols of the formula

HOCHRCH$_2$OH by the base hydrolysis of an alkylene carbonate of the formula

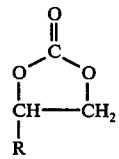

in which each R is either hydrogen or methyl, which comprises:
 (A) providing the alkylene carbonate in admixture of water, carbon dioxide, alkylene glycol and potassium carbonate catalyst, to form a homogeneous liquid phase mixture;
 (B) providing said mixture in a reaction zone wherein the temperature of said mixture is at least 100° C;
 (C) evolving carbon dioxide from said homogeneous liquid phase mixture;
 (D) separating the potassium carbonate catalyst in a mixture with alkylene glycol from glycol product;

(E) recycling said catalyst-glycol mixture to step (A); and
(F) periodically feeding potassium carbonate catalyst make-up to said catalyst-glycol mixture before it is fed to step (A).

2. the continuous process of claim 1, wherein the potassium carbonate catalyst is utilized in an amount of between about 0.03 to about 10 weight percent, based on the weight of alkylene carbonate fed to the reaction.

3. The continuous process of claim 2, wherein the amount of potassium carbonate catalyst is between about 0.1 to about 5.0 weight percent.

4. The continuous process of claim 3, wherein the amount of potassium carbonate catalyst is between 0.25 and about 1.5 weight percent.

5. The continuous process of claim 1, wherein the temperature of step (B) is between 100° and 300° C.

6. The continuous process of claim 5, wherein the temperature is between about 120° and about 200° C.

7. The continuous process of claim 1, wherein pressure in the reaction zone of step (B) is greater than about 80 psig.

8. The continuous process of claim 7, wherein the pressure is greater than about 80 psig and less than about 2000 psig.

9. The continuous process of claim 8, wherein the pressure is greater than about 80 psig and less than about 750 psig.

10. The continuous process of claim 1, wherein the amount of water combined with the alkylene carbonate is at least one mole of water for each mole of alkylene carbonate.

11. The continuous process of claim 10, wherein the amount of water is at least about 1.2 moles of water to about 10 moles of water for each mole of alkylene carbonate.

12. The continuous process of claim 11, wherein the mole ratio of water is 1.5 to 2.5 moles for each mole of alkylene carbonate.

13. The continuous process of claim 1, wherein the alkylene carbonate is ethylene carbonate.

14. The continuous process of claim 1, wherein the glycol product is ethylene glycol.

15. A continuous process for making glycols of the formula

by the base hydrolysis of an alkylene carbonate of the formula

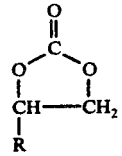

in which each R is either hydrogen or methyl, which comprises:
(A) providing the alkylene carbonate in admixture of water, carbon dioxide, alkylene glycol and potassium carbonate catalyst, to form a homogeneous liquid phase mixture;
(B) providing said mixture in a reaction zone wherein the temperature of said mixture is at least 100° C;
(C) evolving carbon dioxide from said homogeneous liquid phase mixture;
(D) separating the potassium carbonate catalyst in admixture with alkylene glycol from glycol product;
(E) recycling said catalyst-glycol mixture to step (A);
(F) periodically feeding potassium carbonate catalyst make-up to said catalyst-glycol mixture before it is fed to step (A);
(G) separating water from glycol product in step (D); and
(H) recycling said water to step (A).

* * * * *